US006275297B1

(12) United States Patent
Zalicki

(10) Patent No.: US 6,275,297 B1
(45) Date of Patent: Aug. 14, 2001

(54) METHOD OF MEASURING DEPTHS OF STRUCTURES ON A SEMICONDUCTOR SUBSTRATE

(75) Inventor: Piotr S. Zalicki, Sunnyvale, CA (US)

(73) Assignee: SC Technology, Fremont, CA (US)

( * ) Notice: Subject to any disclaimer, the term of this patent is extended or adjusted under 35 U.S.C. 154(b) by 0 days.

(21) Appl. No.: 09/136,462

(22) Filed: Aug. 19, 1998

(51) Int. Cl.$^7$ ........................................ G01B 9/02
(52) U.S. Cl. ........................ 356/496; 356/504; 356/632
(58) Field of Search ................................. 356/496, 498, 356/511, 372, 381, 382, 632, 504

(56) References Cited

U.S. PATENT DOCUMENTS

| 4,674,883 | 6/1987 | Baurschmidt . |
| 5,087,121 | * 2/1992 | Kakuchi et al. ..................... 356/382 |
| 5,212,454 | 5/1993 | Probsting . |

(List continued on next page.)

FOREIGN PATENT DOCUMENTS

JP401235807A * 9/1989 (JP) .
JP402059603A * 2/1990 (JP) .

OTHER PUBLICATIONS

Irving P. Herman, "Optical Diagnostics for Thin Film Processing," Academic Press, 1996, pp. 352–479; pp. 481–489; pp. 715–738.

"A Virtual Interface Method for Extracting Growth Rates and High Temperature Optical Constants from Thin Semiconductor Films Using in situ Normal Incidence Reflectance", W.G. Breiland and K.P. Killeen, Journal of Applied Physics, vol. 78, No. 11, American Institute Of Physics, Dec. 1995.

(List continued on next page.)

Primary Examiner—Samuel A. Turner
(74) Attorney, Agent, or Firm—Sierra Patent Group, Ltd.; Andrew V. Smith

(57) ABSTRACT

A method and apparatus are provided for measuring a depth geometry of a structure on a semiconductor substrate including a plurality of recessed and non-recessed portions, wherein one of the recessed and non-recessed portions includes a reference interface and one of the recessed and non-recessed portions has a dielectric layer thereon. A broadband light source irradiates the substrate and a detector detects a first spectral component comprising light reflected from the non-recessed portions, a second spectral component comprising light reflected from the recessed portions, and a third spectral component comprising light reflected from the dielectric layer. Spectral reflectance information of the detected rays is stored and a plot of reflectance intensity versus wavelength is generated. A depth geometry of one of the recessed portions and the dielectric layer are determined relative to the reference interface, based on an interferometric analysis of the plot. The depth geometries are determined with a resolution as low as 100 angstroms. The method may be performed in-situ. The dielectric layer may be a photoresist layer above the silicon substrate, or oxide filling the recess. The analysis for determining the depth geometries preferably includes fitting the plot to a reflectance model, wherein $$\text{Reflectance}=C_1<|E_R|^2>/<|E_0|^2>+C_2<|(E_R+E_T)|^2>/<|E_0|^2>+C_3<|E_T|^2>/<|E_0|^2>+C_4;$$

and $E_0$ is the amplitude of the incident broadband light source, $E_R$ is the amplitude of the first component, $E_T$ is the amplitude of the second component, $<|E_R|^2>/<|E_0|^2>$ describes light reflected from the non-recessed portions, $<|E_T|^2>/<|E_0|^2>$ describes light reflected from the recessed portions, $<|(E_R+E_T)|^2>/<|E_0|^2>$ is an interference component describing light reflected from both the recessed and non-recessed portions, $C_1$, $C_2$, and $C_3$ describe relative weights of the first, second and interference components of the reflectance, respectively and $C_4$ describes light scattered from sides of the trenches.

40 Claims, 2 Drawing Sheets

U.S. PATENT DOCUMENTS

| | | |
|---|---|---|
| 5,341,205 | 8/1994 | McLandrich et al. . |
| 5,452,953 | 9/1995 | Ledger . |
| 5,563,084 | 10/1996 | Ramm et al. . |
| 5,807,761 | 9/1998 | Coronel et al. . |

OTHER PUBLICATIONS

"Trench Depth Measurement System for VLSI RAM's Capacitor Cells Using Optical Fiber and Michelson Interferometer", K. Takada, K. Chida, J. Noda, and S. Nakajima, Journal of Lightwave Technology, vol. LT–5, No. 7, IEEE/OSA, Jul. 1987.

* cited by examiner

METHOD OF MEASURING DEPTHS OF STRUCTURES ON A SEMICONDUCTOR SUBSTRATE

BACKGROUND OF THE INVENTION

1. Field of the Invention

The invention relates to a technique for measuring depth geometries on a semiconductor substrate, and particularly to determining depth geometries of recesses and dielectric layers relative to a reference interface at high resolution by detecting reflected rays of an incident broadband light source and determining the depth geometries based on an interferometric analysis of a measured dependence of reflectance intensity on wavelength.

2. Discussion of the Related Art

Many techniques have been developed for measuring thin film thicknesses and depths of structures on semiconductor substrates. Among the most widely practiced of them is Fourier Transform Infrared Spectroscopy (FTIR). See, e.g., Takada, et al., Trench Depth Measurement System for VLSI DRAM's Capacitor Cells Using Optical Fiber and Michelson Interferometer, Journal of Lightwave Technology, Vol. LT-5, No. 7, 881 (July 1987). Transmission and reflection spectroscopy may be performed using this technique.

The trench depth measurements performed by Takada et al. are on substrates having trenches wherein reflections from only two interfaces, the trench bottoms and the non-recessed silicon substrate, are detected and a wavelength spacing between peaks of an interferogram is measured to determine the depth of the trenches relative to the silicon substrate surface. The technique is not a satisfactory method of measuring trench depth, however, when a dielectric layer is either in the trench or over the silicon substrate. A measurement of the wavelength spacing between peaks in this case yields an indeterminate trench depth value because a reflection component from the dielectric surface changes the measured peak spacing in the interferogram. This peak spacing change, in turn, causes the trench depth to be measured relative to a "virtual" interface lying at an unknown depth different from either of the silicon substrate or dielectric layer surfaces.

Moreover, when the dielectric layer thickness is changing, the wavelength spacing between the peaks of the interferogram will change as the dielectric layer thickness changes, yielding a changing trench depth value, even when the trench depth is not actually changing. When the trench depth is changing along with the thickness of the dielectric layer, the peak spacing change will yield a trench depth change rate which differs from that which is actually occurring. Since it is important to know trench depths with respect to interfaces of known depth having one or more dielectric layers of unknown thickness above them, a more satisfactory technique is needed.

Additionally with respect to conventional FTIR techniques, they do not have sufficient resolution to accurately measure shallow trench depths. In fact, a minimum detectable trench depth using the technique of Takada et al., e.g., is approximately 1.5 microns with an error of +/−0.2 microns. This is because, as mentioned, Takada et al. merely calculates a frequency spacing between adjacent peaks in their FTIR spectra to determine trench depths. Furthermore, FTIR techniques such as those performed by Takada et al. cannot achieve better resolution without using a far broader band incident radiation source. Finally, FTIR techniques such as those performed by Takada et al. do not work well when additional layers are formed on the silicon substrate because overlapping frequencies erode the resolution of the technique further.

Another technique for measuring layer thicknesses and trench depth uses a monochromatic light source to irradiate a trench bottom or a layer on a substrate, and plots the reflected intensity versus time. See, e.g., W. G. Breiland and K. P. Killeen, *A Virtual Interface Method for Extracting Growth Rates and High Temperature Optical Constants from Thin Semiconductor Films Using In Situ Normal Incidence Reflectance*, J. App. Phys. 78 (11), pp. 6726–36 (December 1995). As the layer thickness or trench depth changes, the plot passes through a periodic series of maxima and minima whose temporal positions depend on the thickness or trench depth at any given time. When measuring trench depths, however, this technique does not take into consideration a changing thickness of a dielectric layer above a fixed interface, such as, e.g., a photoresist layer above a silicon substrate or an oxide layer in a recess. Moreover, the measurement cannot be performed instantaneously.

A technique for performing microdensitometric measurements of linewidths and spectral interferometric measurements of thicknesses is disclosed in U.S. Pat. No. 4,674,883 to Baurschmidt. The technique is designed particularly for measuring line widths, rather than depths. Baurschmidt discloses to scan the surface of a wafer using a collecting lens to gather scattered light. The collecting lens gathers light reflected at a wide range of reflection angles. Gathered light is focused to a slit, spectrally dispersed and detected by a position sensitive array detector. The technique exhibits a resolution of around 10 microns due to the large numerical aperture of the lens and wide range of detected reflection angles of detected reflected rays. The resolution of this technique is not satisfactory for performing depth measurements of structures such as shallow trenches and recesses.

Profilometry techniques have been used to measure thicknesses of thin films. A stylus in contact with a surface is drawn over a step at the edge of a thin film and the step height measured. Depths of wide structures such as wide trenches and/or recesses may also be measured, but limitations on the size of the stylus used to perform the technique restrict applicability of the technique, so that depths of narrow structures such as narrow trenches are not measurable. Moreover, profilometry is a mechanical, rather than an optical technique, and contact by the stylus disturbs structures and films on a silicon substrate when measurements are performed.

Today shallow trench isolation (STI) is the preferred method for isolating MOS-transistors and other devices on silicon. STI allows smaller structure processing than its predecessor, localized oxidation of silicon (LOCOS), which relied upon a complex process including initially growing silicon dioxide on a silicon substrate. An illustration of the STI technique is shown in FIG. 1. When the trenches 2 are filly etched (not as shown), they will reach thousands of angstroms into the silicon substrate. The trenches 2 will serve to isolate transistor devices on a completed chip, because the trenches 2 will be filled with insulating material. Most typically, a material such as oxide is deposited into the trench 2 to fill the trench 2 and electrically isolate devices on either side of it.

Before etching of the trench structures 2 begins, a layer of photoresist 4 is formed. A stepper next photolithographically exposes portions of the photoresist to ultraviolet radiation in a predetermined pattern. A developer is next poured on to remove either the exposed or non-exposed portions of the photoresist. A dry etch next removes material not protected by photoresist, i.e., under places where the photoresist was removed in the developing step. In principle, this etching step etches, e.g., the trenches, above which no photoresist layer remains, while leaving unscathed the photoresist layer and material beneath it. However, during a real dry etching process, the photoresist layer is also stripped away, albeit at a slower rate than the depth of the trenches is increased. This is why a satisfactory trench depth measurement technique will ultimately measure a trench depth with respect to a fixed interface beneath the photoresist layer, rather than with respect to the air/photoresist interface 7.

Trench depths may be first measured with respect to the air/photoresist interface 7. Thereafter, a Thickness of the photoresist layer may be subtracted, and the result taken to be the distance from the bottom of the trench to the bottom of the photoresist layer. To do this accurately, a precise thickness of the photoresist layer 4 must be determined. Since the photoresist layer thickness changes during the etch, unless the photoresist layer thickness can be measured at the time of the trench depth measurement, the accuracy of any trench depth determination will be unsatisfactory. For shallow trenches, the accuracy of the photoresist layer thickness measurement is even more important than it is for deeper structures.

Poly recess on oxide processing is another prevalent technique wherein accurate recess depth determinations are desired. Recess structures are first etched into an oxide layer. Next, a layer of poly is deposited onto the oxide to both fill the recesses and to form a planar layer of poly over the oxide. A subsequent etch then first strips away the planar poly. Then, both the oxide and the poly filling the recesses is etched. At this time, the poly and the oxide are etched at different rates. It is desired to have a technique for measuring the recess depth and the oxide layer thickness, each with respect to a fixed interface such as the silicon substrate or the poly.

SUMMARY OF THE INVENTION

The present invention solves the aforementioned problems and satisfies the aforementioned desires by providing a method and apparatus for measuring depth geometries of structures on a semiconductor substrate including a plurality of recessed and non-recessed portions, wherein the non-recessed portions include a reference interface and at least one of either the recessed or non-recessed portions has a dielectric layer thereon. A broadband light source irradiates the recessed and non-recessed portions. A detector detects reflected light including a first spectral component comprising light reflected from the recessed portions and a second spectral component comprising light reflected from the non-recessed portions, wherein at least one of the first and second components further comprises a third component comprising light reflected from the dielectric layer. Spectral reflectance information of the detected rays is stored and a plot of reflectance intensity versus wavelength is generated. Depth geometries of the recesses and the dielectric layer are determined relative to the at least one reference interface based on an interferometric analysis of the plot. The depth geometries are determined with a resolution of less than one micron, or 100 nanometers, or less. The method may be performed in-situ. In one example, the dielectric layer is a photoresist layer above the silicon substrate and the recess is a trench such as a shallow trench for isolating transistor devices. In another example, the dielectric layer is oxide filling a recess in a poly recess on oxide process. The analysis for determining the depth geometries preferably includes fitting the plot to a reflectance model, wherein $$\text{Reflectance} = C_1 <|E_R|^2>/<|E_0|^2> + C_2 <|(E_R+E_T)|^2>/<|E_0|^2> + C_3 <|E_T|^2>/<|E_0|^2> + C_4;$$

and $E_0$ is the complex amplitude of the incident broadband light source, $E_T$ is the amplitude of the first component, $E_R$ is the amplitude of the second component, $<|E_R|^2>/<|E_0|^2>$ describes light reflected from the non-recessed portions, $<|E_T|^2>/<|E_0|^2>$ describes light reflected from the recessed portions, $<|(E_R+E_T)|^2>/<|E_0|^2>$ is an interference component describing light reflected from both the recessed and non-recessed portions, $C_1$, $C_2$, and $C_3$ describe relative weights of the first, second and interference components of the reflectance, respectively, and $C_4$ describes light scattered from sides of the trenches.

DETAILED DESCRIPTION OF THE PREFERRED EMBODIMENT

The technique of the present invention is applicable to any of a variety structures on a semiconductor wafer. Structural depths and thicknesses may be measured on many types of structures and layers including a wide variety of dielectrics and a wide variety of recess types relatively positioned in a wide variety of locations on the wafer due to different processing techniques performed on the semiconductor wafer. Below, we describe particular wafer processing variations wherein the present invention advantageously determines structural depths and/or layer thicknesses with high resolution. However, it is not intended that the invention be limited to the examples set forth here. It is intended that only the appended claims set forth the metes and bounds of the present invention.

Generally, we begin with a semiconductor substrate having a plurality of recessed and non-recessed portions. An example of a recessed portion is a deep or shallow trench. A dielectric layer is formed either in the recess or over the non-recessed portion. Examples of dielectric layers include a photoresist layer over the non-recessed portions and an oxide layer in the recessed portions. Depth geometries of the recessed portions and the dielectric layer with respect to a reference interface are determined using the technique of the present invention.

Figure 1:
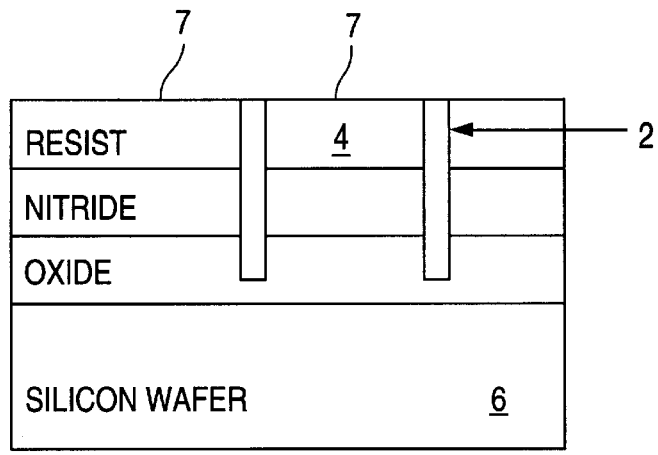
FIG. 1 illustrates a substrate being processed with a conventional trench isolation technique.
Figure 2:
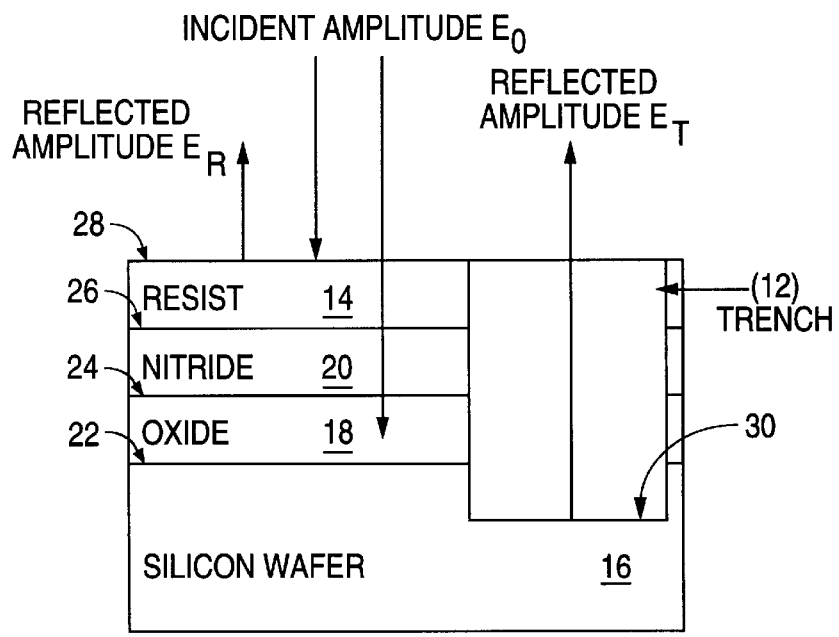
FIG. 2 illustrates a substrate similar to that of FIG. 1, but after a longer etch, such that the trench is deeper and the resist layer is thinner, and wherein depth geometries of the trench and resist layer are being measured according to the present invention.

FIG. 2 illustrates a substrate being processed with a conventional trench isolation technique wherein depth geometries of the trench 12 and resist layer 14 are being measured according to the present invention. To arrive at the processing stage of the substrate of FIG. 2, a conventional silicon wafer 16 is first prepared. A layer of oxide 18 is next deposited and a layer of nitride 20 is deposited after that. A resist layer 14 is deposited on the nitride 20, wherein the resist layer 14 is patterned in such a way tat there is no resist over those portions of the nitride 20 through which it is desired to dry etch a trench 12. The technique utilizes photolithographic exposure to an ultraviolet light source such as that from an excimer laser.

When the substrate is first exposed to the dry etching process, both the nitride 20 and the resist 14 layers are etched away. The nitride 20 is etched at a much faster rate, however, owing to the patterning of the photoresist layer 14. After the nitride 20 is etched, the oxide 18 is etched, again at a faster rate then the photoresist 14. After the oxide 18 is etched, the silicon wafer 16 itself is etched, once again at a faster rate than the photoresist 14. For example, the silicon 16 may be typically etched at a rate of 42 Å/sec and the photoresist 14 at a rate of 16 Å/sec. After some etching into the silicon 16, we arrive at the substrate of FIG. 2.

During the etching process, neither the oxide 18, the nitride 20, nor the silicon 16 beneath the photoresist 14 is etched, except for minor lateral etching via sides of the trenches 12. Therefore, the silicon/oxide interface 22, the oxide/nitride interface 24 and the nitride/photoresist interface 26 each remain at the same depth throughout the photolithographic process. Moreover, the relative spacings between these interfaces 22, 24 and 26, i.e., the layer thicknesses, are known. These interfaces 22, 24 and 26 can thus each be used as reference interfaces.

The air/photoresist interface 28 and the air/silicon interface 30, i.e., at the bottom of the trench 12, exhibit changing depths as each of the photoresist 14 and the silicon 16 at the bottom of the trench 12 are etched. Also, the relative positions of each of the air/photoresist interface 28 and the air/silicon interface 30 change constantly throughout the etch process with respect to each other and with respect to the reference interfaces 22, 24 and 26.

Figure 3:
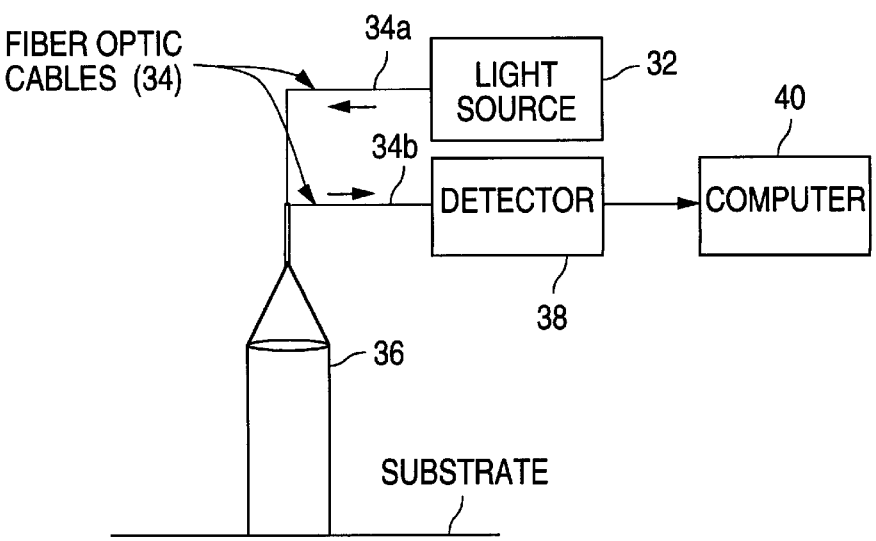
FIG. 3 shows an apparatus for performing depth measurements in accordance with the present invention.

Referring to FIG. 3, during a depth measurement process according to the present invention, a broadband light source 32 irradiates the substrate having incident amplitude $E_0$. Preferably, rays from the light source 32 first enter a first end of a first fiber optic cable 34a having a diameter of between 200 and 600 microns, travel down the cable 34a and exit the other end which is directed at the silicon substrate. Also preferably, the rays exit the first fiber optic cable 34a and are collimated with a lens 36 such that each then normally impinges upon the substrate. At each interface 22–30, some rays are reflected and others are transmitted, such that a quantity of light is detected after being reflected from each interface 22–30. Moreover, interference occurs between rays of the same wavelength reflected from different interfaces 22–30 due to differences in the optical path lengths traversed by the rays.

Rays reflected from each of the reference interfaces 22, 24 and 26, the air/photoresist interface 28 and the trench bottom 30 are detected by a detector 38. Preferably, the rays first encounter a focusing lens 36 which focuses the rays onto a first end of a second fiber optic cable 34b. The fiber optic cable 34b is again from 200–600 microns in diameter. Preferably only rays that had reflected from an interface 22–30 of the substrate substantially normally enter the second fiber optic cable 34b. After the rays travel down the fiber optic cable 34b, they exit the other end and enter the detector 38. The detector is capable of discriminating between rays of different wavelengths.

Spectral reflectance data, or data of detected intensity as a function of wavelength, are stored, e.g., in the memory of a processor 40. A spectrum of detected intensity versus wavelength can then be generated from data stored in the processor 40.

As mentioned, interference occurs between rays of the same wavelength reflected from different interfaces. Depending on the optical path difference between the rays, more or less constructive or destructive interference will occur. It is this interference phenomenon that allows us to determine the relative positions of the interfaces and thus to calculate the depths of recesses such as the trench 16, e.g., and the thicknesses of dielectric layers such as the photoresist layer 14, e.g. Advantageously, the present invention provides a technique for determining the depth of the recesses as well as the thickness of the dielectric layer according to the method set forth below.

Figure 4:
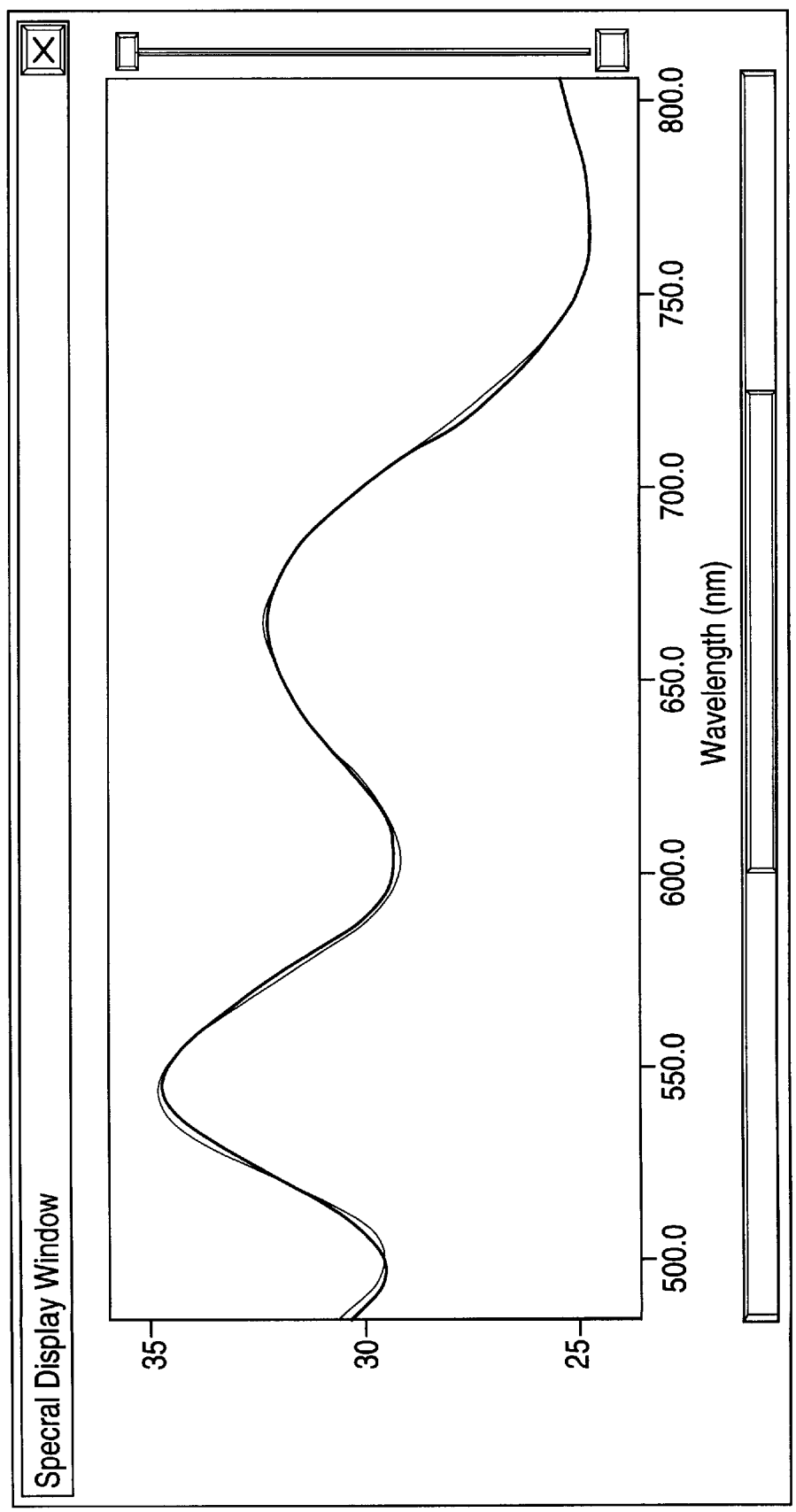
FIG. 4 shows a model spectrum overlying a measured reflectance spectrum illustrating a high correlation therebetween in accordance with the present invention.

FIG. 4 provides an exemplary plot of reflectance intensity versus wavelength generated from data stored by a processor as received from the spectrally discriminating detector described above. Generally, the plot of reflectance intensity versus wavelength is fit to a reflectance model. The model contains parameters corresponding to the depth of the recesses 12, the thickness of the resist layer 14, and the thicknesses of each of the oxide layer 18 and the nitride layer 20. The depth of the recess 12 is first determined relative to the top of the resist layer 14. The thickness of the resist layer 14, as extracted from the fit of the plot to the reflectance model, is then subtracted from the first determined recess depth, to obtain a useful recess depth determined relative to one of the reference interfaces.

As discussed, some prior art techniques simply consider rays reflecting from the recess bottoms 30 and the top 28 of the resist layer 14, From this determination, it is not possible to know the precise recess depth, unless the photoresist thickness is also precisely determined. The present invention provides this determination of the photoresist thickness, which is then subtracted from the recess depth determined relative to the top 28 of the photoresist layer 14, to yield an absolute recess depth determination.

Referring back to FIG. 2, in an exemplary process of the present invention, light of amplitude $E_0$ incident at a 90° angle to the plane of the wafer reflects normally from the wafer surface. The reflected beam is conceptually divided into two components: a component $E_R$ reflected from the resist/nitride/oxide film stack, or interfaces 22, 24, 26 and 28, and a component $E_T$ reflected from the trench bottom 30. Both amplitudes $E_R$ and $E_T$ are defined at the resist layer top plane. Therefore $E_R$ is a function of the resist thickness $d_r$, the nitride thickness $d_n$, and the oxide thickness $d_o$, and $E_T$ is a function of the trench depth $d_t$ from the resist/air interface 28. The complex amplitudes $E_R$ and $E_T$ are described in detail below, but are generally derived from the standard Fresnel and light propagation equations.

Optical properties of dielectric materials are characterized as having complex indices of refraction n=N+iK. N is the refractive index that defines the speed of light in the material and K is the extinction coefficient that defines absorption of light in the material. A normal incidence reflectivity at an interface of two materials with indexes of refraction $n_i$ and $n_j$ given by:

$$r_{ij}=(n_i-n_j)/(n_i+n_j). \tag{1}$$

The normal incidence reflectivity of a layer of material $n_j$ placed between materials $n_i$ and $n_k$ is:

$$r_j=(r_{ij}+r_k \exp(+i4\pi n_j d_j/\lambda))/(1+r_{ij}r_k \exp(+i4\pi n_j d_j/\lambda)), \tag{2}$$

where $r_{ij}$ is the reflectivity of the $n_i/n_j$ interface, $r_k$ is the reflectivity of the top surface of the material $n_k$ including the reflectivity of the underlying layers, $d_i$ is the thickness of layer i, $\lambda$ is the wavelength, and $\exp(+i4\pi n_j d_j/\lambda)$ describes propagation of light in material $n_j$. Equation 2 can be used recursively to calculate a reflectivity of an arbitrary layer stack. For the resist/nitride/oxide/silicon stack, the total reflectivity is given by:

$$r_r = (r_{ar} + r_n \exp(+i4\pi n_r d_r/\lambda))/(1 + r_{ar} r_n \exp(+i4\pi n_r d_r/\lambda)),$$

where $$r_n = (r_m + r_o \exp(+i4\pi n_n d_n/\lambda))/(1 + r_m r_o \exp(+i4\pi n_n d_n/\lambda)),$$

and $$r_o = (r_{no} + r_s \exp(+i4\pi n_o d_o/\lambda))/(1 + r_{no} r_s \exp(+i4\pi n_o d_o/\lambda)),$$

and $$r_s = (n_o - n_s)/(n_o + n_s).$$

The indexes a, r, n, o, s refer to air, resist, nitride, oxide, and silicon. The amplitude $E_R = r_r * E_0$.

The silicon trench reflectivity is given by $r_s = (n_a - n_s)/(n_a + n_s)$, and the amplitude $E_T = r_s * \exp(+i4\pi n_a d_t/\lambda)) * E_0$, where $d_t$ is the trench depth relative to the air/resist interface, and $\exp(+i4\pi n_a d_t/\lambda)$ describes light propagation in the trench.

The wafer total reflectance is given by $R = <|E_R + E_T|^2>/<|E_0|^2>$, where $<>$ denotes the ensemble average and the spatial average over the wafer surface. The model used for fitting the generated plot of reflectance versus wavelength described above and shown in FIG. 4 has the form:

$$R = C_1 * <|E_R|^2>/<|E_0|^2> + C_2 * <|E_R + E_T|^2>/<|E_0|^2> + C_3 * <|E_T|^2>/<|E_0|^2> + C_4.$$

In this reflectance model, the $<|E_R|^2>/<|E_0|^2>$ component describes light reflected from the silicon/oxide/nitride/resist stack, the $<|E_T|^2>/<|E_0|^2>$ component describes light reflected from the trench bottom 30, and the $<|E_R + E_T|^2>/<|E_0|^2>$ component is the interference component described above. The $C_1$, $C_2$, and $C_3$ coefficients represent the relative weights or strengths of the reflectivity components. Their values are within 0 to 1 range. The $C_4$ component describes intensity of light scattered from sides of the trench 12.

The adjustable parameters of the model are the coefficients $C_1$, $C_2$, $C_3$, and $C_4$, the resist thickness $d_r$, and the trench depth $d_t$. The parameter values are determined from the best fit of the reflectance model as a function of wavelength to the measured reflectance as a function of wavelength.

The model described above agrees well with wafer reflectances measured over a wide range of trench depths and the resist layer thicknesses. The model is not limited only to the case of resist/nitride/oxide film stacks separated by silicon trenches 12. The basic elements of the model are the amplitudes $E_R$ and $E_T$. These amplitudes represent light reflected from an arbitrary layer stack on the wafer and an arbitrary recess type. For example, the film stack may comprise bare silicon and the recess can be a trench filled with oxide. In this case, the oxide and poly thicknesses would be changing at different rates during the etch, and yet both thicknesses/depths would be determinable using the technique of the present invention.

The film stack may comprise a resist/polysilicon/oxide structure and the recess may reach only to the polysilicon layer. In this case, the recess depth and the resist layer thicknesses would be changing at different rates during the etch, and again the technique of the present invention could determine both absolute thicknesses/depths. It is also possible to include thickness measurements for inner layers on the film stack, such as nitride and oxide layers as in the case described above. Typical ranges of measurable layer thicknesses and recess depths using the technique of the present invention are in range from less than approximately 100 Å to several microns.

What is claimed is:

1. A method of measuring a depth geometry of a structure on a semiconductor substrate including a plurality of recessed and non-recessed portions, wherein one of said recessed and non-recessed portions includes a reference interface, and wherein at least one of said recessed and non-recessed portions has a dielectric layer thereon, comprising the steps of:
   irradiating said recessed and non-recessed portions of the substrate with a broadband light source;
   detecting a first spectral component comprising light reflected from said recessed portions and a second spectral component comprising light reflected from said non-recessed portions, wherein one of the first and second components further comprises a third component comprising light reflected from said dielectric layer;
   storing data including spectral reflectance information of said first, second and third components; and
   determining a depth geometry of said recessed portions relative to said reference interface based on an interferometric analysis of said data including spectral reflectance information of each of said first, second and third components.

2. The method of claim 1, wherein said depth geometries are determined with a resolution of less than one micron.

3. The method of claim 1, wherein said depth geometries are determined with a resolution of less than 100 nanometers.

4. The method of claim 1, wherein said depth geometries are determined with a resolution of less than 100 angstroms.

5. The method of claim 1, wherein said depth geometries are measured in-situ.

6. The method of claim 1, wherein said dielectric layer is a photoresist layer above the non-recessed portions.

7. The method of claim 6, wherein said photoresist layer is a top layer of a stack of layers including at least one of nitride and oxide.

8. The method of claim 1, wherein said dielectric layer is an oxide layer within said recessed portions.

9. The method of claim 1, wherein said broadband light source is a halogen lamp.

10. The method of claim 1, said first and second components are normal to the plane of the substrate.

11. The method of claim 1, wherein said broadband light source irradiates said substrate at substantially normal incidence.

12. A method of measuring a depth geometry of a structure on a semiconductor substrate including a plurality of recessed and non-recessed portions, wherein one of said recessed and non-recessed portions includes a reference interface, and wherein at least one of said recessed and non-recessed portions has a dielectric layer thereon, comprising the steps of:
   irradiating said recessed and non-recessed portions of the substrate with a broadband light source;
   detecting a first spectral component comprising light reflected from said recessed portions and a second spectral component comprising light reflected from said non-recessed portions, wherein one of the first and second components further comprises a third component comprising light reflected from said dielectric layer;

storing data including spectral reflectance information of said first and second components; and determining a depth geometry of at least one of said recessed portions and said dielectric layer relative to said reference interface based on an interferometric analysis of said data, wherein said determining step includes the step of fitting said plot to a reflectance model, wherein $$\text{Reflectance} = C_1 <|E_R|^2>/<|E_0|^2> + C_2 <|(E_R+E_T)|^2>/<|E_0|^2> + C_3 <|E_T|^2>/<|E_0|^2> + C_4;$$

and $E_0$ is the amplitude of the incident broadband light source, $E_R$ is the amplitude of the first component, $E_T$ is the amplitude of the second component, $<|E_R|^2>/<|E_0|^2>$ describes light reflected from the non-recessed portions, $<|E_T|^2>/<|E_0|^2>$ describes light reflected from the recessed portions, $<|(E_R+E_T)|^2>/<|E_0|^2>$ is an interference component describing light reflected from both the recessed and non-recessed portions, $C_1$, $C_2$, and $C_3$ describe relative weights of the first, second and interference components of the reflectance, respectively, and $C_4$ describes light scattered from sides of the recessed portions.

13. The method of claim 12, wherein said depth geometries are determined with a resolution of less than one micron.

14. The method of claim 12, wherein said depth geometries are determined with a resolution of less than 100 nanometers.

15. The method of claim 12, wherein said depth geometries are determined with a resolution of less than 100 angstroms.

16. The method of claim 12, wherein said depth geometries are measured in-situ.

17. The method of claim 12, wherein said first and second components are substantially normal to the plane of the substrate.

18. The method of claim 12, wherein said dielectric layer is a photoresist layer above the non-recessed portions.

19. The method of claim 12, wherein said dielectric layer is a photoresist layer above a layer of poly.

20. The method of claim 12, wherein said dielectric layer is an oxide layer within said recessed portions.

21. The method of claim 12, wherein said recessed portions are trenches.

22. The method of claim 12, wherein said broadband light source is a halogen lamp.

23. An apparatus for measuring depth geometries of structures on a semiconductor substrate including a plurality of recessed and non-recessed portions, wherein one of said recessed and non-recessed portions includes a reference interface, and wherein at least one of said recessed and non-recessed portions has a dielectric layer thereon, comprising:

a broadband light source;

a detector; and a processor for storing spectral reflectance information of a first detected component of light reflecting from said non-recessed portions and a second detected component of light reflecting from said recessed portions, wherein at least one of the first component and the second component further comprises light reflected from said dielectric layer, and for generating a plot of reflectance intensity versus wavelength based on said stored data, and for determining a depth geometry of said recessed portions and said dielectric layer relative to said reference interface based on an interferometric analysis of said plot, and said processor for determining a depth geometry of said recessed portions relative to a first surface of said dielectric layer and extracting a thickness of said dielectric layer from said analysis of said data, such that said depth geometry determination of said recessed portions relative to said reference interface is based on said determination of said depth geometry relative to said first surface of said dielectric layer and on said dielectric layer thickness extracted from said analysis.

24. The apparatus of claim 23, wherein said depth geometries are measured in-situ.

25. The apparatus of claim 23, wherein said dielectric layer is a photoresist layer above the non-recessed portions.

26. The apparatus of claim 23, wherein said dielectric layer is a photoresist layer above a layer of poly.

27. The apparatus of claim 23, wherein said dielectric layer is an oxide layer within said recessed portions.

28. The apparatus of claim 23, wherein said recessed portions are trenches.

29. The apparatus of claim 23, wherein said broadband light source is a halogen lamp.

30. An apparatus for measuring depth geometries of structures on a semiconductor substrate including a plurality of recessed and non-recessed portions, wherein one of said recessed and non-recessed portions includes a reference interface, and wherein at least one of said recessed and non-recessed portions has a dielectric layer thereon, comprising:

a broadband light source;

a detector; and a processor for storing spectral reflectance information of a first detected component of light reflecting from said non-recessed portions and a second detected component of light reflecting from said recessed portions, wherein at least one of the first component and the second component further comprises light reflected from said dielectric layer, and for generating a plot of reflectance intensity versus wavelength based on said stored data, and for determining a depth geometry of at least one of said recessed portions and said dielectric layer relative to said reference interface based on an interferometric analysis of said plot, wherein said processor fits said plot to a reflectance model, wherein $$\text{Reflectance} = C_1 <|E_R|^2>/<|E_0|^2> + C_2 <|(E_R+E_T)|^2>/<|E_0|^2> + C_3 <|E_T|^2>/<|E_0|^2> + C_4;$$

and $E_0$ is the amplitude of the incident broadband light source, $E_R$ is the amplitude of the first component, $E_T$ is the amplitude of the second component, $<|E_R|^2>/<|E_0|^2>$ describes light reflected from the non-recessed portions, $<|E_T|^2>/<|E_0|^2>$ describes light reflected from the recessed portions, $<|(E_R+E_T)|^2>/<|E_0|^2>$ is an interference component describing light reflected from both the recessed and non-recessed portions, $C_1$, $C_2$, and $C_3$ describe relative weights of the first, second and interference components of the reflectance, respectively, and $C_4$ describes light scattered from sides of the recessed portions.

31. The apparatus of claim 30, wherein said depth geometries are determined with a resolution of less than one micron.

32. The apparatus of claim 30, wherein said depth geometries are determined with a resolution of less than 100 nanometers.

33. The apparatus of claim 30, wherein said depth geometries are determined with a resolution of less than 100 angstroms.

34. The apparatus of claim 30, wherein said depth geometries are measured in-situ.

35. The apparatus of claim 30, wherein said first and second components are substantially normal to the plane of the substrate.

36. The apparatus of claim 30, wherein said dielectric layer is a photoresist layer above the non-recessed portions.

37. The apparatus of claim 30, wherein said dielectric layer is a photoresist layer above a layer of poly.

38. The apparatus of claim 30, wherein said dielectric layer is an oxide layer within said recessed portions.

39. The apparatus of claim 30, wherein said recessed portions are trenches.

40. The apparatus of claim 30, wherein said broadband light source is a halogen lamp.

* * * * *